US006655649B2

(12) United States Patent
Panattoni

(10) Patent No.: US 6,655,649 B2
(45) Date of Patent: Dec. 2, 2003

(54) ASSEMBLY FOR CASTING AND USE OF AN ISOELECTRIC FOCUSING STRIP

(75) Inventor: Cory M. Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 10 days.

(21) Appl. No.: 10/095,563

(22) Filed: Mar. 11, 2002

(65) Prior Publication Data

US 2003/0168576 A1 Sep. 11, 2003

(51) Int. Cl.⁷ .............................................. B29C 39/10
(52) U.S. Cl. ............................ 249/97; 249/96; 249/163
(58) Field of Search ........................... 249/96, 97, 160, 249/163

(56) References Cited

U.S. PATENT DOCUMENTS

| 4,415,428 A |   | 11/1983 | Nochumson et al. |
| 5,993,627 A | * | 11/1999 | Anderson et al. ............ 204/456 |
| 6,113,766 A | * | 9/2000 | Steiner et al. ............... 204/606 |
| 6,156,182 A |   | 12/2000 | Olech et al. |
| 6,264,876 B1 | * | 7/2001 | Ballay ......................... 264/509 |

FOREIGN PATENT DOCUMENTS

WO        WO 01/20315 A1 *  3/2001

OTHER PUBLICATIONS

Gorg, A. et al. "The current state of two–dimensional electrophoresis with immobilized pH gradients," Electrophoresis, Apr. 2000, 1037–1053, 21(6).

* cited by examiner

Primary Examiner—James P. Mackey
Assistant Examiner—Donald Heckenberg
(74) Attorney, Agent, or Firm—M. Henry Heines; Townsend and Townsend and Crew LLP

(57) ABSTRACT

Isoelectric focusing gels are cast in a rod-shaped casting mold split longitudinally into two halves, each half having a half-circle profile so that the combined halves form a completed mold that is tubular in shape with a circular cross section. Flat grooves are cut into the flat contacting surfaces of each of the mold halves, the grooves in direct opposition to one another to form a chamber of rectangular cross section extending the full length of the mold and open at both ends. One groove receives a flexible backing strip for the gel and the other serves as the casting chamber for the gel. Once the gel is cast in this mold, isoelectric focusing can be performed as if the gel were a tube gel, and the two mold halves are then readily separated to permit removal of the gel and its transfer if desired to a second dimension separation.

8 Claims, 3 Drawing Sheets

*Fig. 4a*
*Fig. 4b*
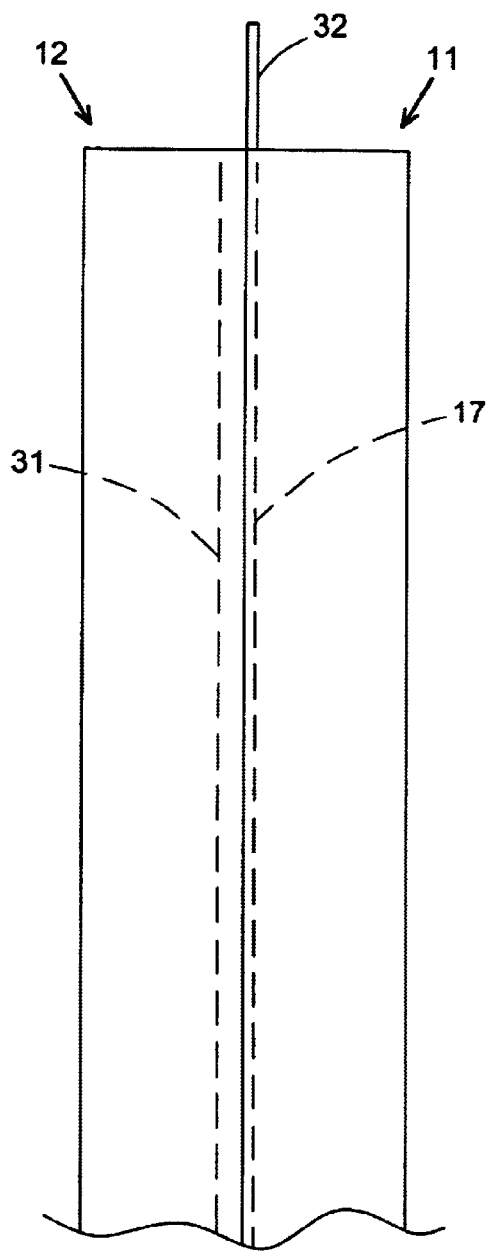
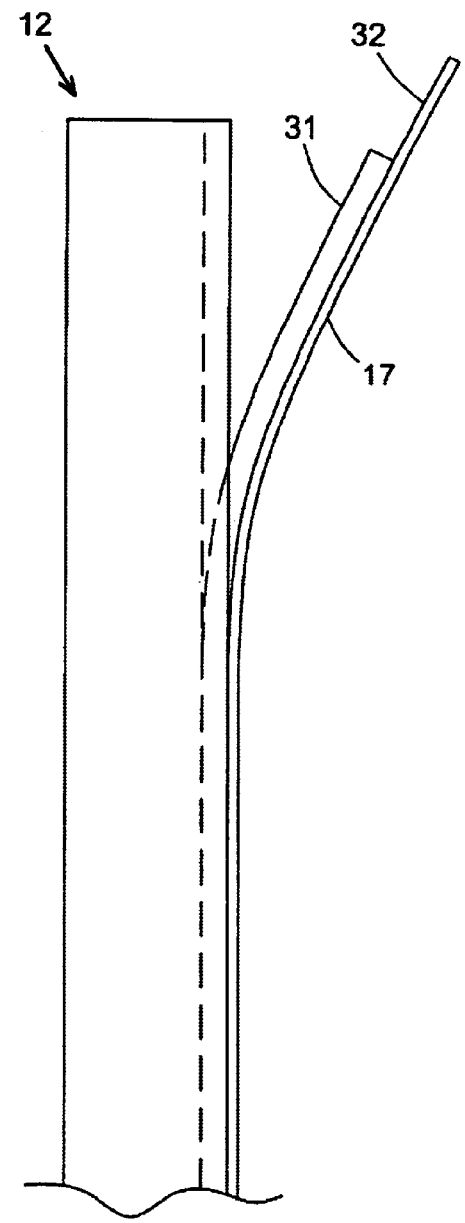

ASSEMBLY FOR CASTING AND USE OF AN ISOELECTRIC FOCUSING STRIP

BACKGROUND OF THE INVENTION

1. Field of the Invention

This invention resides in the field of electrophoretic separation media, and addresses in particular the elongated gel strips used for isoelectric focusing.

2. Background of the Invention

Electrophoresis for purifying proteins and separating complex protein mixtures has developed to the point where it is now performed in many different ways. Variations arise in the composition of the separation medium, the geometrical configuration of the separation medium, the manner in which mobility through the medium is achieved, and the parameter on which separation is based.

One type of electrophoresis that is particularly useful is isoelectric focusing, in which the proteins are separated in a linear manner according to their isoelectric points. Isoelectric focusing is at times used as the entire separation process, and at other times as the first dimension of a two-dimensional separation, the second dimension being performed by placing the linear medium with its isoelectrically focused zones along one edge of a two-dimensional ("slab"-shaped) separation medium. An electric field is then imposed on the two-dimensional medium in a direction transverse to the linear medium, causing migration of the contents of each focused zone out of that medium and into the two-dimensional medium along parallel paths where the contents of each zone are separated according to a parameter other than isoelectric point. The proteins in the original sample thus have the benefit of being separated according to two parameters.

The pH gradient is commonly achieved by using a dimensionally stable medium that consists of a molecular matrix to which functional groups have been attached that are either charged or become charged when the medium is placed in an electric field. Strips of solid media that contain such groups are commonly referred to as "immobilized pH gradient" ("IPG") strips. The composition and structure of these strips are described by Rosengren et al. in U.S. Pat. No. 4,130,470, issued Dec. 19, 1978. The solid material that forms the matrix of the strip is either a granular, fibrous, or membrane material, or a gel. Examples of suitable gels are polyacrylamide, cellulose, agarose, dextran, polyvinylalcohol, starch, and silica gel. The functional groups, which are immobilized on the matrix by covalent bonding or other means, may be positively charged groups such as amino or other nitrogen-bearing groups or negatively-charged groups such as carboxylic acid groups, sulfonic acid groups, boronic acid groups, phosphonic or phosphoric acid groups, or esters of these acids. The typical fabrication procedure for polymeric media is to copolymerize charged or chargeable monomers with uncharged monomers or to include charged crosslinking agents. A monotonic increase or decrease in the concentration of the charged or chargeable groups will produce the desired gradient.

The linear isoelectric focusing medium can be either a tube gel or a flat gel strip, and both have disadvantages. The tube gel must be removed from its tubular enclosure after the first-dimension separation so that the tube gel can be placed in direct contact with the slab gel for the second-dimension separation. Tube gels are difficult to remove from their enclosures, and once removed, are difficult to handle due to their lack of rigidity and the need to minimize contact of the gel with the user's fingers. Strip gels, by contrast, are relatively easily to manipulate since they are not run inside enclosures and are cast over a plastic backing sheet which the user can handle without touching the gel. Nevertheless, strip gels are generally supplied in dehydrated form and must be rehydrated before use. This is generally accomplished with the sample itself (in diluted form) by simply wetting the strip with the sample and allowing both to stand until equilibration is achieved. Among the limitations of this procedure are that the amount of sample that can be absorbed by the gel in this manner is limited by the diffusion process. In addition, care must then be taken to assure that the strip does not lose water to the atmosphere and thereby become dehydrated. To prevent this from happening, the strip is covered with an electrically insulating, water-immiscible liquid such as mineral oil, and kept covered during the isoelectric focusing. During this time, contact of the two ends of the strip with electrodes must be maintained. In addition, once the isoelectric focusing is completed and before the second-dimension separation is begun, the mineral oil must be removed completely since any residual oil may interfere with the electrical continuity between the strip and the slab gel. Removal of the oil can be a difficult and messy procedure. Finally, the equipment used to perform isoelectric focusing on a strip gel is relatively complicated and expensive owing to the configuration of the gel, the manner in which the gel is placed on the equipment, and the manner in which the electrical contacts are made.

SUMMARY OF THE INVENTION

The present invention resides in an assembly in which an isoelectric focusing (IEF) gel can be cast and used, the assembly offering the benefits of both a tube gel and a flat IEF strip and none of the disadvantages. The assembly consists of a rod-shaped casting mold split longitudinally into two halves or half casting molds, each having a half-circle profile so that when the halves are combined along their flat contacting surfaces, the completed mold is tubular in shape with a circular cross section. Grooves or indentations are cut into each of the two contacting surfaces, the grooves in direct opposition to one another to form a chamber of rectangular cross section extending the full length of the mold and open at both ends. One groove receives a flexible backing strip for the gel and the interior of the other, when the two halves are combined, serves as the casting chamber for the gel. The gel once cast in this chamber with the backing strip in place will adhere to the backing strip which can be grasped to remove the gel from the mold.

The circular cross section of the exterior of the combined halves of the assembly permits the assembly to be used in electrophoresis apparatus that is designed for a tube gel, i.e., laboratory instrumentation that is designed to receive a tube gel in its tubular enclosure and to provide the electrical connections to the tube gel that are necessary for electrophoresis to take place. The tube gel shape also permits the gel to be loaded with sample by the enhanced procedures that are used with tube gels, thereby permitting greater sample quantities to be loaded and sample loading to be accomplished in shorter periods of time. The split-mold construction then enables the user to open the assembly after isoelectric focusing is completed and to easily remove and reposition the gel without touching the gel.

In preferred embodiments, the circular cross section extends less than the full length of the assembly, occupying instead only a segment beginning at one end of the assembly, the remaining length being a rectangular cross section to facilitate the sue of screws, clamps, or other means to secure the two halves together in a readily removable manner.

Further features, embodiments, advantages, and implementations of the invention will become apparent from the description that follows.

BRIEF DESCRIPTION OF THE DRAWINGS

FIG. 4a is a side view of the completed assembly shown in the preceding drawings.

FIG. 4b is a side view of one of the two mold halves in the process of having the gel removed after electrophoresis has taken place.

DETAILED DESCRIPTION OF THE INVENTION AND PREFERRED EMBODIMENTS

While this invention is susceptible to considerable variation in terms of structural details such as the arrangement and shapes of the parts and their dimensions, the invention will be best understood by a detailed explanation of one particular embodiment. The drawings attached hereto depict such an embodiment.

Figure 1A:
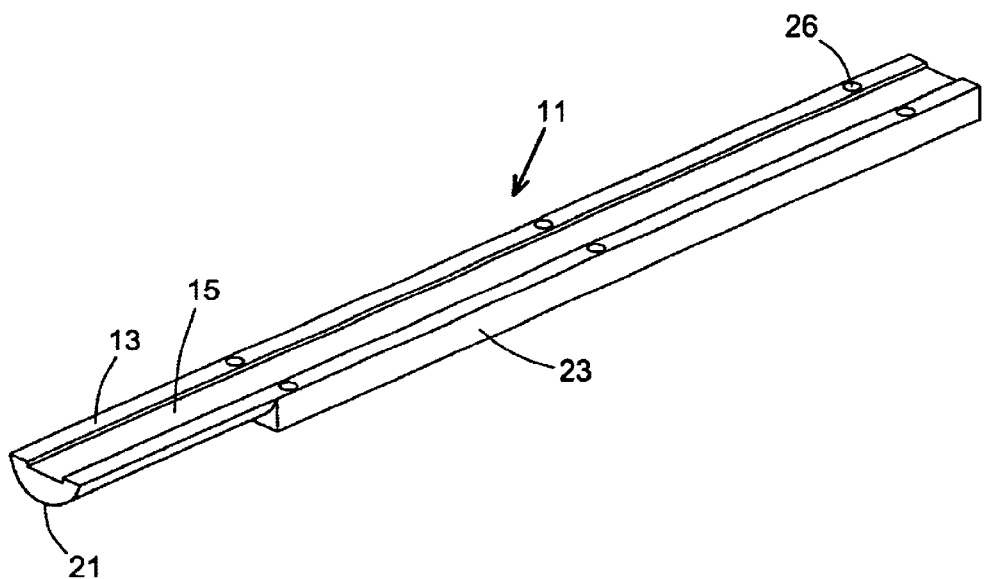
FIGS. 1a and 1b are perspective views of the two half casting molds, respectively, of one example of an assembly in accordance with the present invention.
Figure 1B:
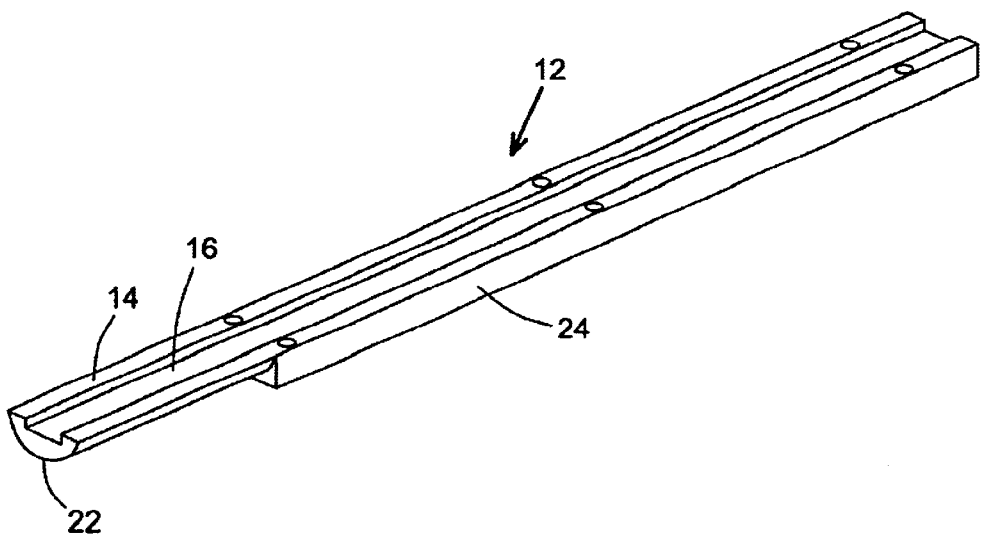
Figure 2A:
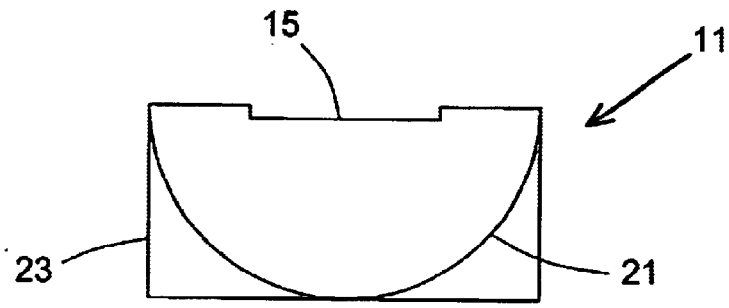
FIGS. 2a and 2b are end views of the two half casting molds shown in FIGS. 1a and 1b, respectively.
Figure 2B:
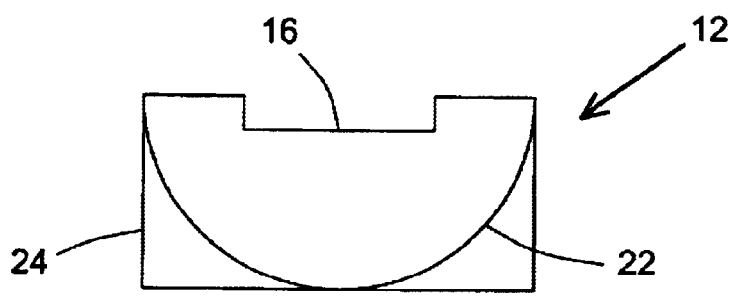

The perspective views of FIGS. 1a and 1b represent the upper half casting mold 11 and the lower half casting mold 12, respectively, each shown with their contacting surfaces 13, 14, turned upward. The contacting surfaces are both flat except for the shallow groove 15, 16 extending lengthwise along the center line of each surface. The grooves and the profiles of each of the half casting molds are more readily visible in the end views of FIGS. 2a and 2b, which show that both grooves have a flat or horizontal floor and an overall rectangular cross section, and the grooves are of unequal depths, the groove 15 in the upper half casting mold 11 being less deep than the groove 16 in the lower half casting mold 12. The shallow groove 15 receives the flexible strip of solid material that supports the gel, while the deep groove 16 serves as the gel casting chamber. The two grooves may be of equal width or may differ in width. In the latter case, the groove 15 for the support strip may be slightly wider than the groove 16 for the gel.

Figure 3:
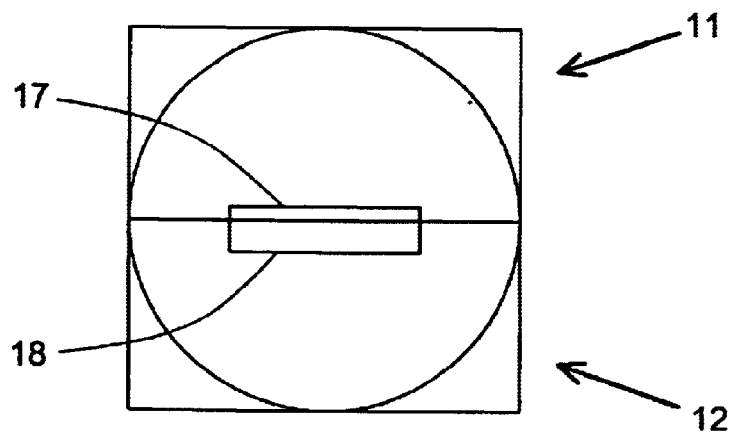
FIG. 3 is an end view of the two half casting molds of FIGS. 1a and 1b combined to form the completed assembly.

FIG. 3 shows the two half molds combined to form a completed mold and gel enclosure ready for sample loading and isoelectric focusing. To achieve this configuration, the flexible strip 17 (which is shown in FIG. 3) is first placed in the shallow groove 15 of the upper half mold 11, and the upper half mold is then turned face down to place the two flat surfaces in contact. The rest of the chamber formed by the two mated grooves is then filled with gel-forming solution and the gel is cast.

The forward ends of the half molds each have semicircular profiles 21, 22, as both the perspective views (FIGS. 1a and 1b) and the end views (FIGS. 2a and 2b) illustrate. Thus, when the mold is fully assembled as shown in FIG. 3, the outer contour is that of a circular cross-section tube. This circular cross section enables the user to insert the assembly, with gel inside, in an electrophoresis apparatus designed for tube gels, such as the various PROTEAN electrophoresis cells manufactured by Bio-Rad Laboratories, Inc., Hercules, Calif., USA. The remainders of the half molds have rectangular profiles 23, 24, and this portion of the assembled mold is therefore rectangular in cross section. The particular example shown in the drawings has a square cross section. The purpose of the change in cross section is to facilitate the securing of the two half molds together, since rectangular shaped halves are more easily secured together by screws, bolts, or clamps. The example shown in the drawings has six sets of screw holes 26. Alternative means of securing the two halves together in a readily releasable or openable fashion will be apparent to those skilled in the art. Examples are clamps, snap fittings, friction fittings, and non-permanent adhesives. In addition, although the two halves as shown are fully separable, they may alternatively be joined by hinges, pivot connections, or strips of flexible material.

Casting of the gel in the assembled mold and loading of the gel with sample are performed according to conventional techniques. Electrophoretic sample loading, i.e., the loading of a sample by placing the sample at one end of the gel and imposing an electric current along the length of the gel to drive the sample into the gel, is particularly convenient and useful. Once the sample is loaded, isoelectric focusing can proceed by conventional techniques.

After electrophoretic separation has occurred, the mold halves are separated and the gel is extracted, either for direct analysis or for placement along the edge of a slab gel for further separation as the second dimension of a two-dimension separation. Removal of the gel from the mold is illustrated in FIGS. 4a and 4b. The side view of FIG. 4a shows the assembled mold halves in an upright position. The gel 31 is shown by a dashed line in the lower mold half 12 which is on the left of the assembly in this view, and the flexible support strip 17 is shown by a dashed line in the upper mold half 11 on the right. One end 32 of the support strip protrudes from the end of the mold.

When the separation is terminated, the mold halves are separated as shown in FIG. 4b, leaving the lower mold half 12 with the gel 31 inside and the support strip 17 adhering to the gel. The user grasps the free end 32 of the support strip to pull the gel out of its groove.

The materials used in the practice of this invention are not critical to the invention itself and can vary. Gels of any of the compositions noted above can be used, although polyacrylamide and agarose gels are the most common. Polyacrylamide gels are particularly preferred in view of their widespread use. The flexible support strip 17 can be any material that supports and adheres to the gel without interfering with the separation properties of the gel. Preferred support strips are those that couple with the gel material, such as agarose or acrylamide, during the gel polymerization process. A description of support materials of this type is found in Nochumson, S., et al., U.S. Pat. No. 4,415,428, "Support for Electrophoresis and Method of Producing Same," issued Nov. 16, 1983, the contents of which are incorporated herein by reference in their entirety. Materials meeting this description are available commercially from FMC Bioproducts, Rockland, Me., USA, under the product name GelBond film (for agarose gels) and Gelbond PAG® film (for polyacrylamide gels). The molds themselves can be formed of any rigid material that is inert and preferably readily moldable. Plastics such as polycarbonate and acrylics are examples.

The dimensions of the molds are likewise noncritical to the invention and can vary. In most cases, it is contemplated that the grooves will have depths within the range of from about 0.01 cm to about 0.10 cm, and widths within the range of from about 0.1 cm to about 1.0 cm, and the circular cross section segment of the mold assembly will have a length of from about 2.0 cm to about 5.0 cm in length and a diameter of from about 0.5 cm to about 2.5 cm (which will also be the length of one side of the square cross section segment). The total length of the mold may range from about 10 cm to about 30 cm. In a presently contemplated example, the total length is 18 cm, the length of the circular section is 3.8 cm, the diameter of the circular section and the length of one side of the square section is 0.9 cm, the shallow groove has a depth of 0.02 cm and a width of 0.33 cm, and the deep groove has a depth of 0.05 cm and a width of 0.30 cm, all approximate.

The foregoing is offered for purposes of illustration. Further variations and modifications that still embody the concepts that are fundamental to this invention as expressed above will be readily apparent to those skilled in the art.

What is claimed is:

1. An enclosure for an isoelectric focusing gel, said enclosure comprising:

first and second elongate half casting molds, each half casting mold having a half-circle profile and a flat contacting surface, said half casting molds when placed in contact along said flat contacting surfaces forming a tubular casting enclosure of circular cross section;

each half casting mold having an indentation in said flat contacting surface and extending the length thereof;

a flexible strip of inert solid support material sized to fill the indentation in one of said half casting molds; and means for removably securing said half casting molds together.

2. An enclosure in accordance with claim 1 in which said indentations are of rectangular cross section.

3. An enclosure in accordance with claim 2 in which said indentations are of rectangular cross section and of different depths.

4. An enclosure in accordance with claim 2 in which said indentations are from about 0.01 cm to about 0.10 cm in depth.

5. An enclosure in accordance with claim 1 in which said flexible strip has a resin adhered to one side thereof which bonds to an acrylamide or agarose gel.

6. An enclosure in accordance with claim 5 in which said resin adhered to said flexible strip bears ethylenically unsaturated groups that couple with acrylamide monomers during polymerization of such monomers within said enclosure to form a polyacrylamide gel.

7. An enclosure in accordance with claim 1 in which said circular cross section extends the length of a terminal segment of said tubular casting enclosure, and each said half casting mold further comprises a segment having a rectangular profile thereby providing said tubular casting enclosure with a rectangular cross-section segment adjacent to said terminal segment, and said means for removably securing said half casting molds together reside in said rectangular cross-section segment.

8. An enclosure in accordance with claim 7 in which said terminal segment is from about 2.0 cm to about 5.0 cm in length, and said rectangular cross-section segment is from about 5.0 cm to about 20 cm in length.

* * * * *